United States Patent [19]

Kipperman

[11] Patent Number: 5,092,839
[45] Date of Patent: Mar. 3, 1992

[54] CORONARY THROMBECTOMY

[76] Inventor: Robert M. Kipperman, 501 E. 87th St., Apt. 8A, New York, N.Y. 10128

[21] Appl. No.: 414,981

[22] Filed: Sep. 29, 1989

[51] Int. Cl.⁵ .............................................. A61B 17/22
[52] U.S. Cl. .......................................... 604/53; 604/96; 606/159; 606/194; 128/898
[58] Field of Search ............... 606/127, 108, 192, 193, 606/194, 196, 200, 159; 604/96, 101, 53, 264; 128/898

[56] References Cited

U.S. PATENT DOCUMENTS

| | | | |
|---|---|---|---|
| 668,879 | 2/1901 | Miller | 606/127 |
| 3,435,826 | 4/1969 | Fogarty . | |
| 3,467,101 | 9/1969 | Fogarty et al. | 128/348 |
| 3,635,223 | 1/1972 | Klieman . | |
| 4,030,503 | 6/1977 | Clark, III . | |
| 4,109,659 | 8/1978 | Sheridan | 128/349 |
| 4,195,637 | 4/1980 | Gruentzig et al. | 128/348 |
| 4,271,839 | 6/1980 | Fogarty et al. | 128/344 |
| 4,315,512 | 2/1982 | Fogarty | 128/344 |
| 4,422,447 | 12/1988 | Schiff | 128/1 |
| 4,448,195 | 5/1984 | Leveen et al. | 128/344 |
| 4,476,866 | 10/1984 | Chin | 128/344 |
| 4,479,497 | 10/1984 | Fogarty et al. | 128/344 |
| 4,483,340 | 11/1984 | Fogarty et al. | 128/344 |
| 4,493,711 | 1/1985 | Chin et al. | 604/271 |
| 4,526,175 | 7/1985 | Chin et al. | 128/344 |
| 4,531,943 | 7/1985 | Van Tassel et al. | 604/280 |
| 4,551,292 | 11/1985 | Fletcher et al. | 604/280 |
| 4,561,439 | 12/1985 | Bishop et al. | 128/348.1 |
| 4,564,014 | 1/1986 | Fogarty et al. | 128/344 |
| 4,606,347 | 8/1986 | Fogarty et al. | 128/344 |
| 4,611,594 | 9/1986 | Grayhack et al. | 606/127 |
| 4,630,609 | 12/1986 | Chin | 128/344 |
| 4,655,748 | 4/1987 | Mushika | 604/96 |
| 4,762,130 | 8/1988 | Fogarty et al. | 28/348 OL |
| 4,776,337 | 10/1988 | Palmaz | 606/108 |
| 4,787,899 | 11/1988 | Lazarus | 606/108 X |
| 4,994,032 | 2/1991 | Sugiyama et al. | 606/194 |

FOREIGN PATENT DOCUMENTS

| | | | |
|---|---|---|---|
| 156202 | 10/1985 | European Pat. Off. | 606/159 |
| 2057636 | 3/1972 | Fed. Rep. of Germany | 606/127 |

Primary Examiner—Michael H. Thaler
Attorney, Agent, or Firm—Kenyon & Kenyon

[57] ABSTRACT

The present invention is directed to a method and apparatus for removing thrombus and plaque from a coronary artery which is at least partially occluded due to deposits of plaque and thrombus on the inner wall or the artery. More particularly, the invention provides a treatment method and apparatus for the same, wherein a balloon catheter and coronary thrombectomy catheter are inserted into an at least partially occluded coronary artery. The coronary thrombectomy catheter with the balloon catheter are placed upstream from the occluded area. A balloon at the distal end of the balloon catheter is inflated, expanding the distal end of the coronary thrombectomy catheter. The balloon is then deflated, the distal tip of the guide catheter retaining its expanded shape. The balloon is deflated and extended beyond the occluded portion of the artery. The balloon is then re-expanded and retracted toward the expanded distal end of the guide catheter carrying with it, residual pieces of thrombus and/or plaque which had been dislodged from the artery wall, the balloon forming a plug at the distal end of the coronary thrombectomy catheter so that the apparatus containing the thrombus and plaque may be removed form the artery. The balloon also may be used to perform an angioplasty procedure.

11 Claims, 3 Drawing Sheets

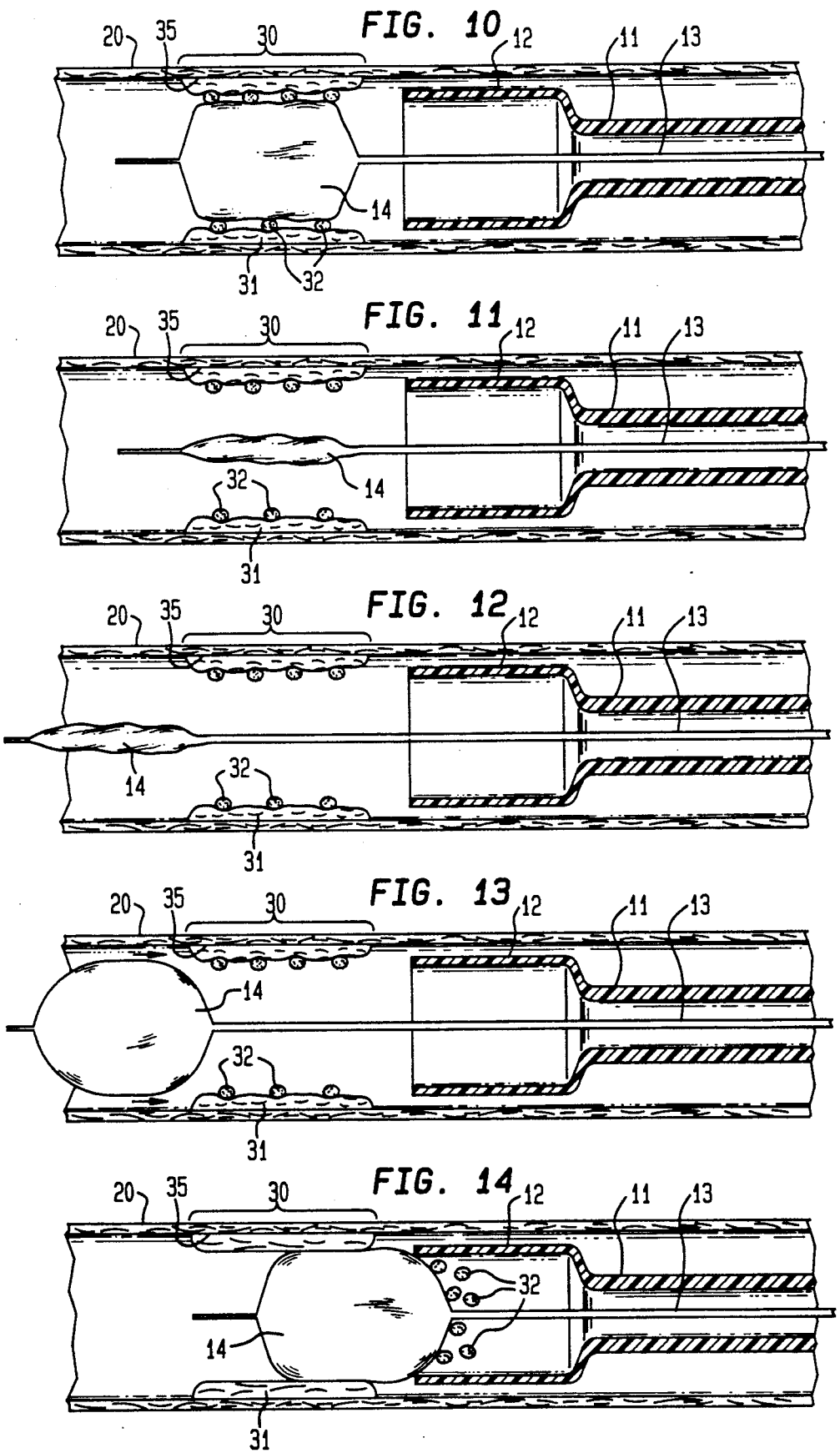

CORONARY THROMBECTOMY

FIELD OF THE INVENTION

The present invention is directed to a method and apparatus for removing thrombus and plaque from a coronary artery which is at least partially occluded due to deposits of plaque and thrombus on the inner wall of the artery.

BACKGROUND AND SUMMARY OF THE INVENTION

Coronary angioplasty has been used as an alternative to coronary bypass surgery to open occluded coronary arteries supplying blood to the heart muscle. Balloon catheters have been used to perform the angioplasty procedure. In such a procedure, the balloon catheter is inserted into an artery and guided into a coronary artery to a portion of the coronary artery which has been at least partially occluded by deposits of plaque and thrombus on the artery wall. The balloon catheter is inflated at the occluded portion of the artery, opening the passageway. Ordinarily, the catheter is then removed from the artery.

The present invention is based upon the recognition that pieces of thrombus may form at anytime on the plaque.

When angioplasty is performed, the thrombus may dislodge and travel further into the artery, eventually causing blood clots or blockage in other portions of the artery. The thrombus may continue to form where the angioplasty was performed thus causing further blockage at the portion of the artery which was originally occluded. The present invention permits removal of thrombus from the artery, thereby lowering the risk of future blockage.

Techniques have been used to remove thrombus from arteries remote from the heart as for example in the femoral artery. In such a procedure, typically, the balloon catheter is withdrawn in its inflated state directly out of an artery, thus carrying and removing thrombus with it, and, because of the direction of the flow of blood, without any danger of the thrombus traveling to superior arteries. Because a coronary catheter is guided into a coronary artery by way of the aorta, attempting to remove the thrombus from a coronary artery simply by withdrawing an inflated balloon catheter would pose serious risks that the dislodged thrombus would be carried by the blood travelling through the aorta to the brain or other parts of the body, causing strokes or partial blockage of other arteries.

It is a primary objective of the present invention to provide a method and apparatus which would allow removal of dislodged thrombus from a coronary artery during a coronary angioplasty or thrombectomy procedure while significantly reducing the risk of carrying the thrombus into the bloodstream where as a result additional blockages, especially in the brain, may occur.

Generally, the coronary thrombectomy apparatus of the invention comprises a balloon catheter with an inflatable balloon at the distal end coupled to an inflator mechanism, and a coronary thrombectomy catheter fitting over the balloon catheter. The balloon catheter and the coronary thrombectomy catheter are arranged to be axially moveable with respect to each other. The distal end of the coronary thrombectomy catheter comprises a material that is sufficiently flexible so that it may be expanded when the inserted balloon of the balloon catheter is inflated, and also sufficiently rigid so that when the balloon of the balloon catheter is deflated, the distal end of the coronary thrombectomy catheter retains its expanded shape. The coronary thrombectomy catheter and balloon catheter may be used together to perform a coronary angioplasty procedure and to remove thrombus and/or plaque from a coronary artery.

Pursuant to a feature of the invention, the coronary thrombectomy catheter may comprise a polymer material such as polyurethane which is thinned at the distal end of the thrombectomy catheter.

In another embodiment, the coronary thrombectomy catheter may comprise a thinned polymer material such as polyurethane, which is covered with a reinforced coating, preferably of glass fibers, for the entire length of the catheter with the exception of the distal end of the thrombectomy catheter.

The balloon catheter which is inserted into the thrombectomy catheter may be inflated so that when it expands, the thinned distal end of the catheter also expands. The balloon catheter has the ability to be deflated, and reinflated. Following expansion of the coronary thrombectomy catheter, the balloon catheter may then be deflated and extended beyond the distal end of the coronary thrombectomy catheter into the artery. The balloon catheter may be guided into the occluded portion of the artery and used to perform an angioplasty procedure, i.e., inflating the balloon to open an occlusion of the artery. Pursuant to a feature of the invention, the balloon catheter would be used to carry thrombus or plaque out of the artery. The balloon is extended beyond the occluded portion, inflated and then retracted toward the expanded distal end of the thrombectomy catheter to dislodge and carry thrombus into the expanded distal end. The balloon catheter may be inflated to a size larger than the inner circumference of the expanded distal end of the coronary thrombectomy catheter so that when the balloon catheter is retracted into the coronary thrombectomy catheter, the balloon acts as a plug, closing the distal end of the coronary thrombectomy catheter and retaining the dislodged thrombus within the coronary thrombectomy catheter.

Generally, the coronary thrombectomy procedure of the invention comprises the steps of inserting a balloon catheter and a coronary thrombectomy catheter with an outer guide catheter into an artery; guiding the balloon catheter and the coronary thrombectomy catheter, within the guide catheter, to an entrance of a coronary artery; extending the coronary thrombectomy catheter and balloon catheter out of the guide catheter into the coronary artery; inflating the balloon catheter to expand the distal end of the coronary thrombectomy catheter; deflating the balloon, the distal end of coronary thrombectomy catheter retaining its expanded shape; optionally guiding the deflated balloon catheter into an at least partially occluded portion of the artery; optionally inflating, deflating, and/or manuevering the balloon as necessary to perform an angioplasty procedure; guiding the balloon catheter, the balloon being deflated, so that the balloon is situated downstream from thrombus and/or plaque which is to be removed; reinflating the balloon to a size at which the balloon may act to plug the open expanded distal end of the coronary thrombectomy catheter; retracting the inflated balloon catheter toward the coronary thrombectomy catheter to dislodge and withdraw thrombus and/or plaque from the artery, into the expanded distal end of the coronary thrombectomy catheter and thus retaining dislodged thrombus and/or plaque in the expanded distal end of the coronary thrombectomy catheter and utilizing the expanded balloon to plug the distal end of the coronary thrombectomy catheter; and thereafter removing the coronary thrombectomy catheter containing the balloon catheter and any thrombus or plaque.

BRIEF DESCRIPTION OF THE DRAWINGS

FIGS. 6-14 illustrate the use of the catheter of FIGS. 1-4 according to the angioplasty and thrombectomy method of the present invention.

DETAILED DESCRIPTION

Figure 1:
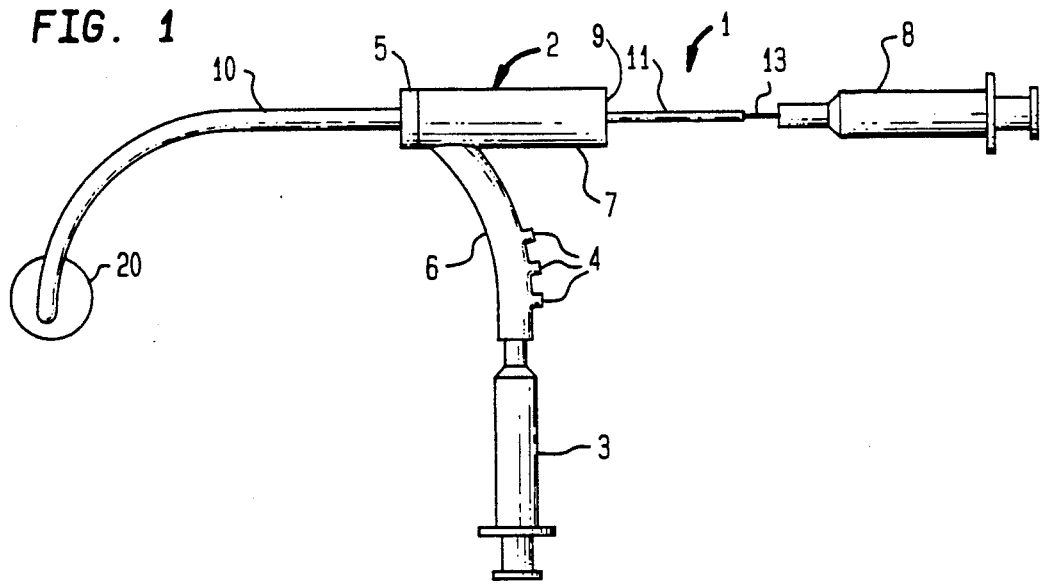
FIG. 1 is a schematic view of a catheter incorporating the features of the present invention.

Referring to FIG. 1, a guide catheter 10 of a coronary thrombectomy apparatus is shown inserted into an artery 20. The guide catheter is coupled by means of a Luer Lok couple 5 to a Y-connector 2. The Y-connector includes a manifold 6 with input valves 4 for coupling to a source or sources of dye, flush, or other fluids for input into the blood stream, as is well known. One of the valves 4 may be connected to a pressure meter (not shown). The manifold 6 is coupled to a syringe 3 to control the ingress and egress of fluids from the valves 4. Through a second leg 7 of the Y connector 2, a hollow coronary thrombectomy catheter 11 containing within, a balloon, catheter 13 is inserted through an aperture valve 9 of the proximal end of the second leg 7 of the Y connector 2. The balloon catheter 13 is coupled with a second syringe 8 connected to the proximal end of the balloon catheter 13. The second syringe 8 is used to control the inflating and deflating of a balloon 14 arranged at the distal end of the balloon catheter 13 as shown in more detail in FIGS. 2-4.

Figure 2:
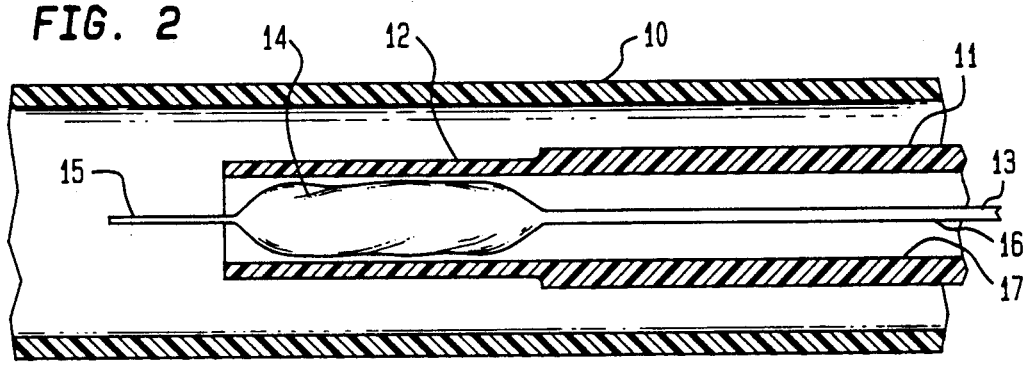
FIG. 2 is a partial side cross-sectional view of the distal end of the catheter of FIG. 1.

FIG. 2 shows an enlarged partial cross section of the distal end of the coronary thrombectomy apparatus illustrated in FIG. 1, which comprises an outer guide catheter 10 through which a hollow coronary thrombectomy catheter 11 is inserted. A balloon catheter 13 is inserted into the coronary thrombectomy catheter 11. The balloon catheter 13 and the coronary thrombectomy catheter 11 are axially moveable with respect to each other and with respect to the guide catheter 10. The coronary thrombectomy catheter 11 includes a distal end 12. The walls 17 of the coronary thrombectomy catheter are made preferably of a polymer such as polyurethane. The walls of the coronary thrombectomy catheter 11 are thinned at approximately the last 2 cm of the distal end 12. The balloon catheter 13 comprises a hollow tubing 16 with a balloon 14 at its distal end and a guide wire 15 at the distal tip of the balloon for guiding the balloon catheter 13 through a coronary artery 20. The proximal end of the balloon catheter 13 is attached to the second syringe 8 as shown in FIG. 1 which controllably introduces fluid under pressure into the hollow tubing 16 and thus causes the balloon 14 to inflate. The fluid may also be withdrawn from the balloon 14 and the hollow tubing 16 by the second syringe 8 thus causing the balloon 14 to deflate.

Figure 3:
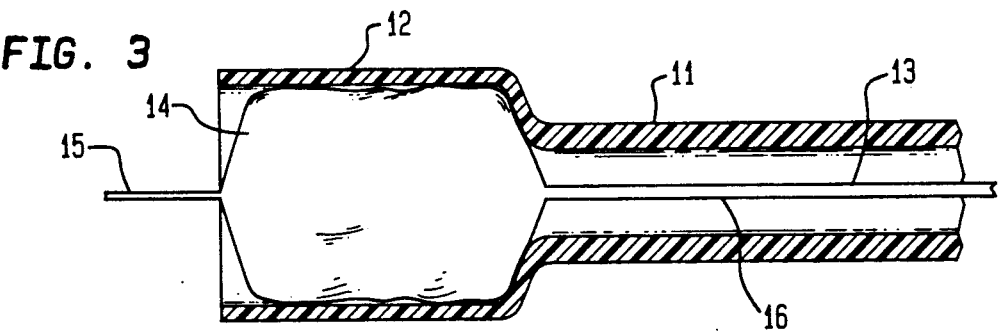
FIG. 3 is a partial side cross-sectional view of the catheter of FIG. 2 illustrating an inflated balloon at the distal end of a balloon catheter to expand the distal end of a coronary thrombectomy catheter.

Referring to FIG. 3, the distal end of the coronary thrombectomy apparatus is shown with the balloon 14 in an inflated state. The coronary thrombectomy catheter, at its thinned distal end 12, is flexible enough such that it is expanded upon inflation of the balloon 14.

Figure 4:
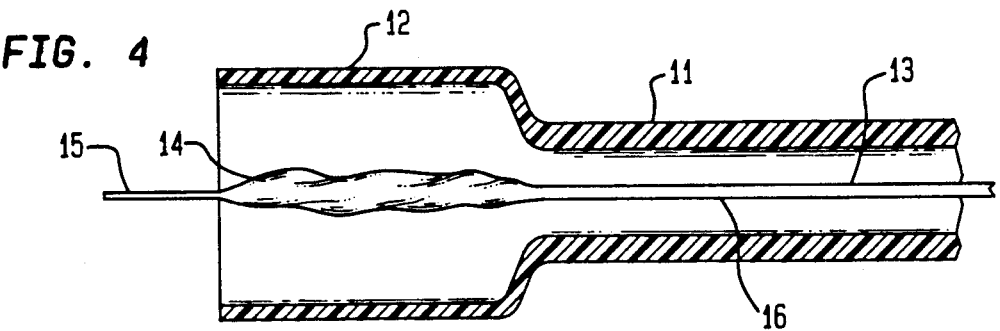
FIG. 4 is a partial side cross-sectional view of the catheter of FIG. 3 illustrating a deflated balloon at the distal end of a balloon catheter within the expanded distal end of a coronary thrombectomy catheter.

Referring to FIG. 4, the distal end of the coronary thrombectomy apparatus is shown with the balloon 14 now in a deflated state. The thinned distal end 12 of the thrombectomy catheter 11 is rigid enough so that it retains its shape upon deflation of the balloon 14.

Figure 5:
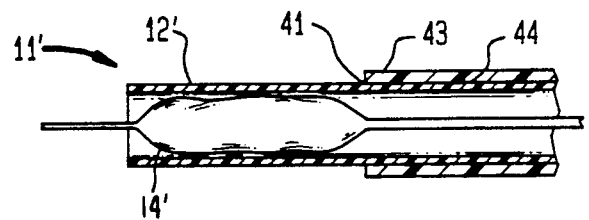
FIG. 5 is a side cross-sectional view of another embodiment of the invention.

FIG. 5 represents another embodiment of the thrombectomy catheter 11' wherein the thrombectomy catheter 11 consists of a thin walled tube 41 which has the same wall thickness throughout it length. The tube 41 has a reinforced coating 43, as for example of glass fibers, extending over the outer wall 44 throughout the length of the tube 21 with the exception of the distal end 12' of the tube 21. The distal end 12' expands upon inflation of the balloon 14', as described above.

FIGS. 6-14 illustrate the steps of the coronary thrombectomy procedure of the invention.

Figure 6:
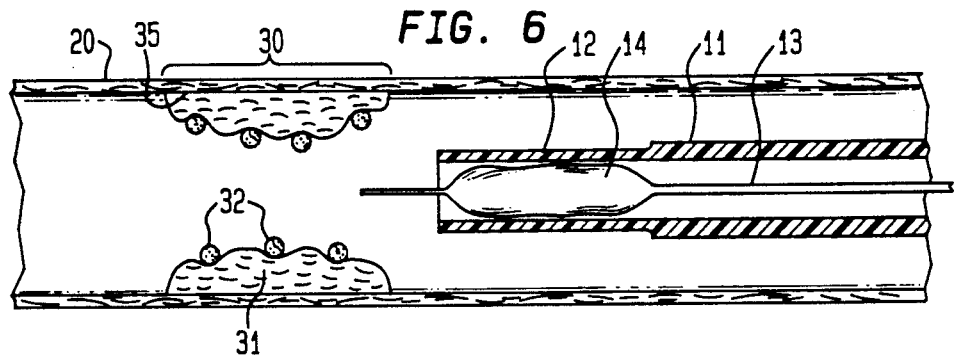

The coronary thrombectomy catheter 11 and the balloon catheter 13 are inserted just upstream of an occluded portion 30 of the artery 20 as illustrated in FIG. 6. The occluded portion 30 has plaque 31 formed on the wall 35 of the artery 20 with thrombus 32 deposited on the plaque 31 and/or the artery wall 35.

Figure 7:
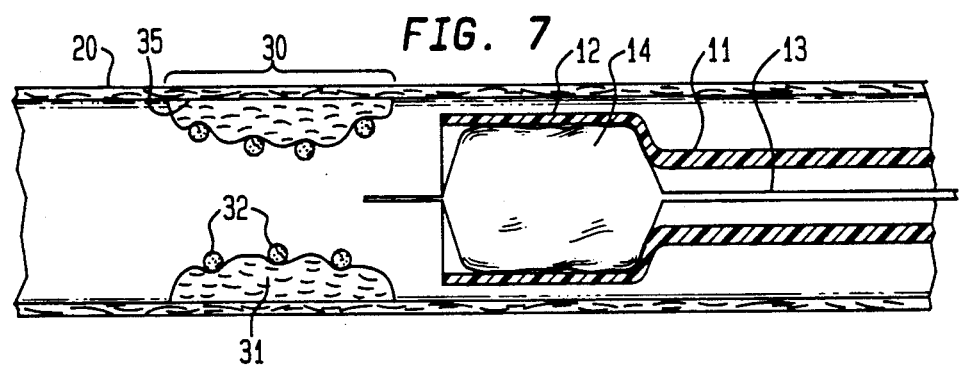
Figure 8:
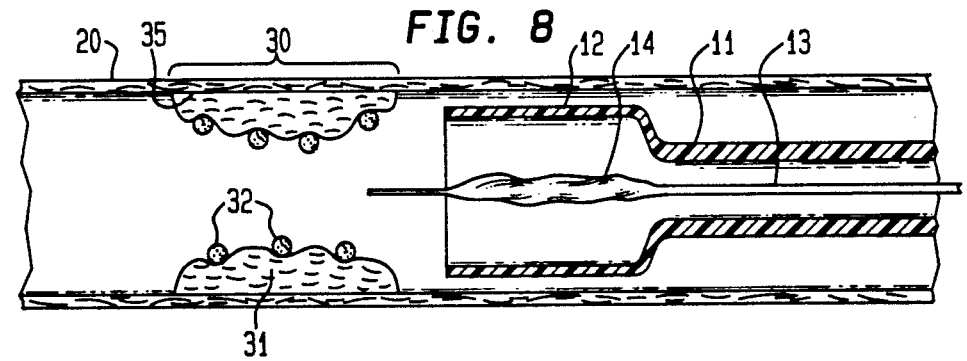

The balloon 14 is inflated thus expanding the distal end 12 of the coronary thrombectomy catheter 11, as illustrated in FIG. 7., the coronary thrombectomy catheter 11 remaining upstream of the occluded portion 30 of the artery 20. The balloon 14 is then deflated as illustrated in FIG. 8, with the distal end of the thrombectomy catheter 11 retaining its expanded shape.

Figure 9:
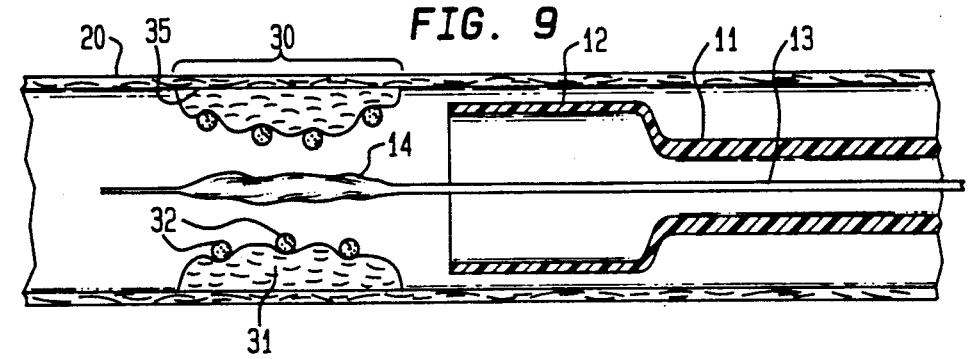

Referring to FIG. 9, the balloon 14 of the balloon catheter 13, with the balloon 14 in its deflated state, is extended out of the coronary thrombectomy catheter 11 and into the occluded portion 30 of the artery 20.

FIG. 10 illustrates the angioplasty procedure wherein the balloon 14, while situated within the occluded portion 30, is expanded to widen the opening of the artery 20. The balloon 14 is then deflated as illustrated in FIG. 11 with the balloon 14 situated within the now opened occluded portion 30 of the artery 20. As illustrated, pieces of thrombus 32 form or remain on the compressed or crushed plaque 31.

FIG. 12 illustrates the second part of the procedure wherein following the angioplasty, the deflated balloon 14 is extended downstream beyond the occluded portion 30 of the artery 20 which has been opened by the angioplasty procedure. As illustrated in FIG. 13, the balloon 14 is positioned so that it may be reinflated and then retracted into the coronary thrombectomy catheter 11, to dislodge and carry with it the thrombus 32 formed on the plaque 31. The dislodged thrombus is moved by the reinflated balloon 14 into the expanded distal end of the coronary thrombectomy catheter 11, as illustrated in FIG. 14. The diameter of the reexpanded balloon 14 is slightly wider that the inner diameter of the expanded distal end 12 of the expanded thrombectomy catheter 11 so that the balloon 14 acts as a plug, sealing the captured thrombus 32 from contact with the blood stream and thus allowing the thrombectomy catheter 11 and balloon catheter 13 to be simultaneously withdrawn from the artery 20 without the risk of the dislodged thrombus 32 being carried away to the brain or other vital areas once the distal end of the apparatus reaches the aorta. Note that the relative size of the expanded distal end of the coronary thrombectomy catheter with respect to the inflated balloon in FIGS. 6–14 is exaggerated for the purpose effect of the balloon acting as a plug when retracted towards the distal end of the coronary thrombectomy catheter.

What is claimed:

1. A method of performing a thrombectomy procedure within a blood vessel comprising the steps of:
   guiding a thrombectomy apparatus upstream of a preselected portion of blood vessel having deposits to be removed, the thrombectomy apparatus comprising a balloon catheter and a thrombectomy catheter, the balloon catheter having a balloon at a distal end of the balloon catheter and being axially moveable within and with respect to the thrombectomy catheter;
   inflating the balloon of the balloon catheter, when the balloon is positioned within a distal end of the thrombectomy catheter;
   providing a material at the distal end of the thrombectomy catheter which comprises a material sufficiently flexible to expand upon inflation of the balloon;
   thereafter deflating the balloon, the material of the thrombectomy catheter being sufficiently rigid so that the distal end retains an expanded shape upon deflation of the balloon;
   extending the balloon catheter downstream from the expanded distal end of the thrombectomy catheter such that the balloon is situated downstream of the preselected portion of the blood vessel having deposits to be removed;
   reinflating the balloon;
   retracting the reinflated balloon towards the expanded distal end of the thrombectomy catheter to dislodge and carry the deposits to be removed into the expanded distal end;
   using the reinflated balloon to plug the expanded distal end; and
   removing the thrombectomy apparatus from the blood vessel.

2. The method of claim 1 further comprising the additional steps of after guiding the thrombectomy catheter upstream of the preselected portion and before using the reinflated balloon to plug the distal end maneuvering the balloon catheter such that the balloon is situated within an occluded portion of the preselected portion blood vessel and inflating the balloon to open the occluded portion of the blood vessel.

3. The method of claim 1, wherein the deposits comprise thrombus.

4. A method of performing a thrombectomy procedure within a blood vessel comprising the steps of:
   guiding a thrombectomy apparatus upstream of a preselected portion of a blood vessel having deposits to be removed, the thrombectomy apparatus comprising a balloon catheter and a thrombectomy catheter, the balloon catheter having a balloon at a distal end of the balloon catheter and being axially moveable within and with respect to the thrombectomy catheter;
   inflating the balloon of the balloon catheter, when the balloon is positioned within a distal end of the thrombectomy catheter;
   providing a material at the distal end of the thrombectomy catheter which comprises a material sufficiently flexible to expand upon inflation of the balloon;
   thereafter deflating the balloon, the material of the thrombectomy catheter being sufficiently rigid so that the distal end retains an expanded shape upon deflation of the balloon;
   extending the balloon catheter downstream from the expanded distal end of the thrombectomy catheter such that the balloon is situated downstream of the preselected portion of the blood vessel having deposits to be removed;
   reinflating the balloon;
   using the reinflated balloon to plug the expanded distal end so that the deposits to be removed become entrapped within the distal end; and
   removing the thrombectomy apparatus from the blood vessel.

5. The method of claim 4 further comprising:
   the additional steps of, after guiding the thrombectomy catheter upstream of the preselected portion and before using the reinflated balloon to plug the distal end, maneuvering the balloon catheter such that the balloon is situated within an occluded portion of the preselected portion of the blood vessel; and
   inflating the balloon to open the occluded portion of the blood vessel.

6. The method of claim 4 wherein the deposits comprise thrombus.

7. A method of removing materials from within a blood vessel comprising the steps of:
   moving a catheter having an interior through the blood vessel to a preselected portion of the blood vessel near the material to be removed;
   moving a balloon catheter through the interior of the catheter, the balloon catheter including a balloon at a distal end thereof;
   inflating the balloon of the balloon catheter when the balloon is positioned within a distal end of the catheter to engage and enlarge the diameter of the catheter at its distal end;
   thereafter, deflating the balloon;
   moving the balloon catheter out from the interior of the catheter to place the deflated balloon at a position on the distal side of the material to be removed;
   inflating the balloon to a diameter sufficient to engage and dislodge the material to be removed and to plug the enlarged distal end of the catheter;
   thereafter using the inflated balloon and the enlarged distal end of the catheter to dislodge and capture the material in the enlarged distal end of the catheter;
   using the inflated balloon to plug the enlarged distal end of the catheter to entrap the dislodged material in the enlarged distal end of the catheter.

8. The method of claim 7, comprising the further step of removing the catheter from the blood vessel with the inflated balloon plugged into the enlarged distal end of the catheter.

9. The method of claim 7, wherein the material is a thrombus.

10. The method of claim 7, wherein the blood vessel is a coronary artery.

11. The method of claim 7, wherein the balloon catheter is initially positioned within the interior of the catheter so that the balloon is at the distal end of the catheter and wherein the step of moving the catheter is carried out by moving the catheter together with the balloon catheter.

* * * * *